(12) United States Patent
Leigh et al.

(10) Patent No.: US 6,605,298 B1
(45) Date of Patent: Aug. 12, 2003

(54) PHARMACEUTICAL COMPOSITIONS AND THEIR USE

(75) Inventors: Steven Leigh, Warlingham (GB); Mathew L. S. Leigh, Warlingham (GB)

(73) Assignee: Phares Pharmaceutical Research N.V., Curacao (AN)

( * ) Notice: Subject to any disclaimer, the term of this patent is extended or adjusted under 35 U.S.C. 154(b) by 0 days.

(21) Appl. No.: 09/655,476

(22) Filed: Sep. 5, 2000

Related U.S. Application Data

(63) Continuation of application No. PCT/GB99/00656, filed on Mar. 5, 1999.

(30) Foreign Application Priority Data

| Mar. 5, 1998 | (GB) | 9804705 |
| Dec. 17, 1998 | (GB) | 9827835 |

(51) Int. Cl.[7] ............................................. A61K 9/127

(52) U.S. Cl. .................... 424/450; 264/4.1; 264/4.3; 264/4.6

(58) Field of Search ................... 424/450, 400, 424/451, 452, 455, 456, 463, 1.21, 9.321, 9.51, 417, 94.3; 428/402.2; 264/4.1, 4.3, 4.6

(56) References Cited

U.S. PATENT DOCUMENTS

| 4,239,754 A | * | 12/1980 | Sache |
| 5,009,956 A | * | 4/1991 | Baumann |
| 5,043,164 A | * | 8/1991 | Huang |
| 5,053,217 A | * | 10/1991 | Lehigh |
| 5,141,674 A | * | 8/1992 | Leigh |
| 5,178,875 A | * | 1/1993 | Lenk |
| 5,707,648 A | * | 1/1998 | Yiv |

FOREIGN PATENT DOCUMENTS

| EP | 0242812 B1 | 10/1987 | .......... A61K/47/10 |
| EP | 0795585 A1 | 8/1997 | .......... C09B/61/00 |
| GB | 505983 | * 5/1939 | |
| GB | 505983 | 6/1939 | |
| GB | 2315216 A | 1/1998 | .......... A61K/9/107 |
| WO | WO 92/18103 | 10/1992 | .......... A61K/9/127 |
| WO | 94/26254 | * 11/1994 | |
| WO | 97/40838 | * 11/1997 | |
| WO | WO 98/02184 | 1/1998 | .......... A61K/47/24 |
| WO | WO 98/58629 | 12/1998 | .......... A61K/9/107 |

* cited by examiner

*Primary Examiner*—Gollamudi S. Kishore
(74) *Attorney, Agent, or Firm*—Burns, Doane, Swecker & Mathis, LLP

(57) ABSTRACT

The invention provides a composition for delivering at least one biologically active compound to a living organism, said composition comprising at least one micelle-forming membrane lipid

54 Claims, 1 Drawing Sheet

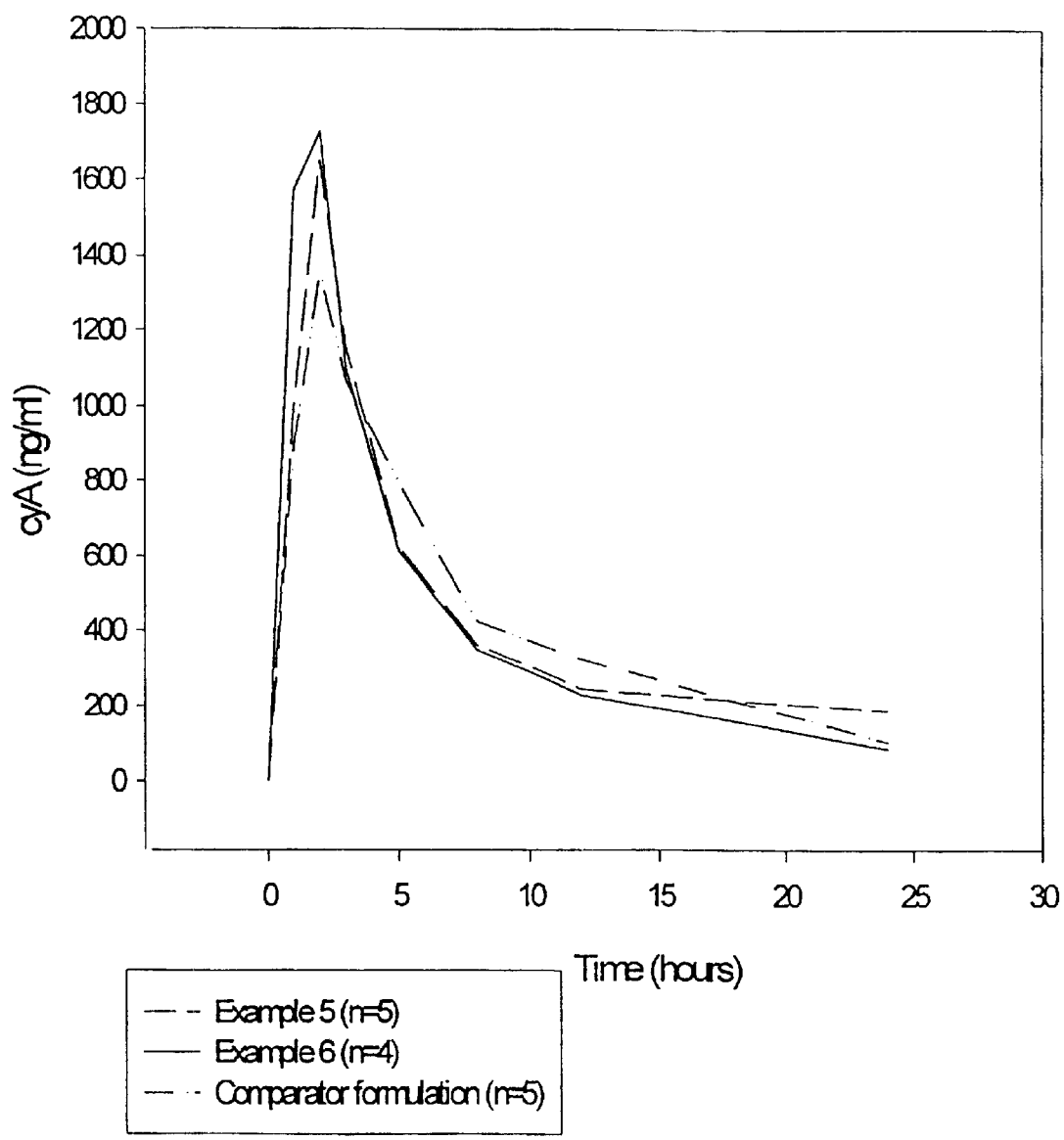

PHARMACEUTICAL COMPOSITIONS AND THEIR USE

CROSS-REFERENCE TO RELATED APPLICATIONS

This application is a continuation of International Patent Application No. PCT/GB99/00656, filed on Mar. 5, 1999, which in turn is an international filing of Great Britain Application No. 98 04705.3, filed on Mar. 5, 1998, and Great Britain Application No. 98 27835.1, filed on Dec. 17, 1998, all of which are incorporated herein by reference.

FIELD OF THE INVENTION

The present invention relates to pharmaceutical compositions useful as carriers to transport biologically active materials in general. More specifically, it relates to novel phospholipid-drug formulations having improved bioavailability, less variability, low toxicity and ease of use either as liquids or as unit dosage forms filled into gelatin capsules or the like.

BACKGROUND

The Problem of Bioavailability

The ultimate goal in drug delivery is clinical efficacy, which can only be achieved when an optimal amount of drug is available in the systemic circulation, the target organ or tissue. In the specific case of oral delivery, it is a requisite for the drug to be adequately absorbed from the gastrointestinal (GI) tract to give good and consistent bioavailability. Many biologically active compounds are 'problem' drugs that have poor and variable oral bioavailability, resulting in lack of efficacy. In many cases this is due to physical factors such as high molecular weight, poor aqueous solubility, or biological factors manifested in low membrane permeability.

Generally, drug absorption and the membrane permeability of drugs are strongly influenced by lipophilicity although polarity and H-bonding of the molecule may also play their part. The more lipophilic the drug, the more easily it partitions into biological membranes. The presence of lipophilic groups, however, leads to marked decreases in aqueous solubility and hence drug concentration at membrane surfaces. This, in turn, leads to lowered uptake and bioavailability. It is generally accepted that lipophilic compounds with molecular weights above about 600 have poor aqueous solubility.

Modern drug discovery programs based on combinational chemistry and high through-put screening methods to identify active compounds are biased towards the selection of lipophilic entities because of the non-aqueous solvents used to solubilise the compounds for screening. It has been reported that about 40% of active compounds coming out of drug discovery programs are lipophilic actives that have poor bioavailability.

Poor absorption is not exclusive to lipophilic compounds. Some hydrophilic compounds e.g. peptides may also have low membrane permeability due to their polar nature and their large molecular size. There is as yet an unfulfilled requirement for safe and effective formulation approaches which improve the bioavailability and decrease variable absorption of poorly absorbed compounds without structural modification of the active molecule. This applies to both lipophilic and hydrophilic compounds.

Bioavailability of Macrolides

Macrolides such as tacrolimus, rapamycin, cyclosporin and their derivatives are examples of fungal metabolites that have poor bioavailability due to erratic and unpredictable uptake from the gastro-intestinal tract. For example, the oral bioavailability of tacrolimus is reported to vary between 5% to 67%. Furthermore, the bioavailability of sub-optimally formulated cyclosporin A may be greatly influenced by the presence of food, increasing from about 30% to 60%. Rapamycin is also a 'problem' drug which is difficult to formulate in oral dosage forms because of poor bioavailability. As a class, these compounds have a variety of pharmacological properties, of which immunosuppression is presently the most important clinically. Other clinical applications that are currently under investigation include modification of multi drug resistance, anti-viral and anti-fungal properties. The most widely used drug for preventing xenograft rejection is cyclosporin A.

Cyclosporins are hydrophobic neutral cyclic peptides with essentially similar chemical and physical properties. Cyclosporin A (cyA) is representative and is the best known example. CyA is widely used in organ transplants to prevent rejection and as an immunosuppressive agent in the treatment of systemic and local auto-immune disorders in which T cells play a major role. CyA has also been used to treat chronic conditions such as rheumatoid arthritis, asthma and non-malignant skin disorders. A cyclosporin derivative eg. PSC 833 is known to modify multi-drug resistance with cytotoxic drugs.

There are two commercially available forms of cyA called Sandimmune and Neoral. Sandimmune (see Swiss Patent 641356) is a solution of cyA in olive oil and ethanol which is emulsified in water using a polyethoxylated oleic surfactant. It suffers from the disadvantage that absorption is incomplete and variable. Neoral can give consistent absorption but relies on potentially harmful synthetic surfactants to form micro emulsions which require a lipophilic phase.

Phospholipids and Their Use

The use of phospholipids in the form of liposomes as vehicles of drug delivery is well established both in the patent and scientific literature. The limitations of the use of pre-formed liposome preparations has been extensively reviewed (see EP-A-0158441) and need not be recapitulated here.

Many of these limitations can be overcome by the use of phospholipid mixtures in a hydrophilic medium, described as pro-liposome compositions to carry active compounds as first disclosed in EP 0158441. These latter compositions comprise blends of bilayer forming diacyl phospholipids, which on dilution with aqueous fluids formed closed vesicular structures with high entrapment of a biologically active compound. WO 88/06438 discloses similar compositions to the above, and claims desalted charged diacyl lipids in a non aqueous water miscible medium. EP-A-0030577 discloses a method of preparing liposomes using mixtures of diacyl phospholipids dissolved or dispersed in a non-volatile hydrophilic medium.

Following these disclosures, there have been many examples which rely essentially on diacyl phospholipids, or lecithin, to improve the delivery of active compounds. Thus EP 0648494 A1 mentions the use of lecithin solutions as a major component, to deliver rapamycin and its derivatives. Similarly, WO 98/40094 describes binary pharmaceutical compositions of a cyclosporin compound, where lecithin or diacyl phospholipids is an auxiliary component.

Departing from the reliance on diacyl phospholipids to carry biologically active compounds, WO 98/58629 discloses substantially homogenous compositions for human administration comprising a biologically active lipophilic compound dissolved in or associated with at least one micelle-forming lipid e.g. monoacyl phosphatidylcholine, or blends of monoacyl phosphatidylcholine with diacyl phosphatidylcholine. The compositions were shown to be surprisingly effective in solubilising and improving the bioavailability of compounds that have poor or variable absorption.

EP 0256090 discloses the use of a specific monoacyl phospholipid species, namely monoacyl phosphatidylethanolamine and a hydrophobic compound, in the form of a micellar suspension at a pH between 8.2 to 14, for intravenous and other injectable purposes.

The use of dilute solutions containing 0.625% w/v MAPC which has 10 or more carbon groups in their fatty acid chain for enhancing the nasal delivery of insulin has also been reported in Pharm Res., Vol 11, No. 11, 1994 p 1623–1630.

PRESENT INVENTION

An object of this invention is to improve the bioavailability and consistency in absorption of either lipophilic or hydrophilic compounds.

Another object of the invention is to reduce variable absorption of lipophilic and hydrophilic compounds.

A further object of this invention is to improve the bioavailability of active compounds in liquid, semi-solid or gel-like formulations.

A further object of this invention is to provide an efficient, effective and non-toxic carrier for compounds that have poor bioavailability eg. cyA where poor solubility would undoubtedly be a factor which prevents the compound being transported in molecular dispersion to the absorption surfaces in the GI tract.

The present invention concerns a further development of the compositions disclosed in co-pending patent application WO 98/58629, in a liquid form. The compositions in this invention can mimic partially digested food mixtures, allowing for higher absorption of 'problem' compounds compared to compositions that only rely on diacyl phospholipids.

One feature of the invention is that the present formulations contain at least one micelle forming monoacyl membrane lipid either alone or preferably in combination with one or more bilayer-forming diacyl membrane lipids. The compositions are characterised by the presence of an effective amount of the monoacyl component dissolved or dispersed in a hydrophilic medium.

The invention provides a composition for delivering at least one biologically active compound to a living organism, said composition comprising at least one micelle-forming membrane lipid characterised in that the composition contains at least one hydrophilic material in an amount effective to render the composition into a liquid, gel or semi-solid which has the property of yielding dispersed lipid aggregates upon contact or further dilution with an aqueous medium.

The invention further provides a liquid pharmaceutical composition comprising:
(a) a mixture of membrane lipids which comprises a micelle-forming lipid and preferably a bilayer-forming lipid;
(b) at least one hydrophilic medium to mobilise the lipids; and optionally
(c) at least one biologically active compound.

The invention further provides a liquid pharmaceutical composition comprising:
(a) a mixture of membrane lipids which comprises firstly a micelle-forming lipid and secondly a bilayer-forming lipid;
(b) water in an amount which is effective to hydrate the lipid mixture; and
(c) at least one biologically active compound.

The invention will be further discussed mainly in terms of oral applications. The formulation principles involved, however, are of general applicability and it should be appreciated that the compositions described are equally suitable for a wide range of other applications.

The above compositions may be formulated so as to be flowable at room or alternatively at elevated temperature for filling into gelatin capsules. The composition may also optionally contain polymers which influence the dispersibility characteristics of the composition on exposure to water or aqueous solutions. Other excipients and stabilisers such as organic thickeners, antioxidants, flavourings, antimicrobial agents, buffering agents, colouring agents and sweetening agents may also be included. The inclusion of surfactants and small amounts of oils as minor components is not excluded. Similarly, membrane stabilisers such as cholesterol, dicetyl phosphate, stearyl amine and other charged amphipathic compounds may be added to the compositions to improve stability.

The formulations may exhibit remarkably good storage stability. They are normally liquid or gel-like presentations at room temperature and may be used as such or filled into unit dosage forms e.g. soft gelatin capsules. Alternatively, the compositions are fluids at elevated temperatures that harden on cooling to room temperature. Such formulations are suitable for filling into hard gelatin capsules or the like as a liquid at temperatures not exceeding about 70° C., solidifying to a plug inside the shell at room temperature.

Lipophilic drugs such as cyA and other compounds can be solubilised in solutions of at least one monoacyl lipid (e.g. MAPC), preferably with diacyl lipids (e.g.PC) in a hydrophilic medium. The reason for the use of such mixtures is three-fold. Firstly, such mixtures can solubilise much higher amounts of lipophilic bioactive compounds such as cyA, than diacyl lipids alone. Secondly, the presence of the monoacyl lipid influences the internal structure and improves the stability of these mixtures, particularly in the presence of water. Thirdly, the bioavailability of cyA may be greatly improved because of better retention at the absorption surfaces and enhanced mucosal penetration due to the presence of MAPC. However, it must not be construed that these are the only reasons.

On contact with water or other aqueous medium, or upon dilution in such media, the compositions have the potential to hydrate. Depending on the precise composition and desired application, the preparations may remain substantially intact in the form of a bolus or disperse rapidly, or more gradually, to form lipid aggregates. The term lipid aggregates is used here to describe a combination of vesicular and non-vesicular structures e.g. liposomes, and various species of micelles and mixed micelles.

Dispersibility and the different types of aggregate structures formed depend on a number of factors e.g. the relative amount and the type of lipid and hydrophilic medium, pH, viscosity and optionally, the presence of other components e.g. polymers and surfactants.

BRIEF DESCRIPTION OF THE DRAWINGS

FIG. 1. Bioavailability of the compositions prepared in Examples 5 and 6, as compared to a control.

DESCRIPTION OF PREFERRED FEATURES

The Lipid Component

The compositions are a mixture of membrane lipid(s), hydrophilic medium and optionally a biologically active compound(s). The membrane lipid component consists of one or more monoacyl membrane derived lipids preferably, but not necessarily, in association with one or more diacyl membrane lipids.

The monoacyl lipid(s) is preferably the monoacyl derivative of a diacyl phospholipid, eg. monoacyl phosphatidylcholine (MAPC), but it can also be the monoacyl derivative(s) of glycolipids, sphingolipids, or another micelle forming phospholipid. The lipids may be derived from natural plant, or animal or microbiological sources, synthesised or partially synthesised including polyethyleneglycol (PEG) derived monoacyl phospholipids, eg. pegalated monoacyl phosphatidylethanolamine.

The diacyl lipid(s) is preferably a phospholipid because such compounds are readily available and tend to be easy to incorporate in the mix. Examples of phospholipids are phosphatidylcholine (PC), phosphatidyl ethanolamine (PE), phosphatidylglycerol (PG), phosphatidylinositol (PI), phosphatidyl serine(PS), phosphatidic acid (PA) and spingomyelin. The acyl chain can either be unsaturated or saturated and can have 12 to 22, preferably 14 to 18 carbon atoms. Other membrane lipids such as glycolipids, ceramides, gangliosides and cerebrosides can be used in place of, or partial place of, phospholipids.

In practice, instead of blending pure fractions of the phospholipids to obtain the target ratios, enzyme modified lecithin (EML), that have the required proportions of the diacyl to the monoacyl fractions are preferred. The term lecithin generally refers to mixtures of bilayer forming diacyl phospholipids substantially free from micelle forming monoacyl phospholipids. When present in purer commercial grades as a by-product during fractionation, the upper limit for monoacyl phospholipids is usually about 1% to 2%. The relative proportions of monoacyl to diacyl lipid can, however, be greatly enhanced by partial hydrolysis of one or more phospholipids e.g. lecithin. Hydrolysis can be chemical or by an enzyme (e.g. phospholipase A2) or by a micro-organism. The phospholipid mixtures which are classed as enzyme modified lecithins (EML) are freely used in foods without restrictions and provide no problems for oral use. Particularly preferred grades of EML used in this invention are refined by solvent extraction or are chromatographically fractionated, or both, free from residual phospholipase A2 activity. The degree of purification or refinement needed will be appropriate for a pharmaceutical grade material and for the degree of stability required for each particular end use. The methods of purification will be familiar to those skilled in the art. Commercial grades of such material may be obtained from Lucas Meyer GmbH. The membrane lipid/lipids employed in the present invention may be:

Mixtures of PC, and MAPC

EML obtained from phospholipase A2 enzyme hydrolysis

Blends of EML with pure PC or MAPC added to obtain the appropriate monoacyl content in the blend.

The total weight of membrane lipid in the composition is usually between 5% to 90% based on the weight of the composition, preferably 20% to 80%, most preferably 40% to 60%, although lesser or greater amounts may be used without departing from the scope of the invention. The molar ratio of the bilayer forming diacyl lipid to the micelle-forming lipid monoacyl lipid in this invention is preferably in the range of 1:5 to 25:1, and is more preferably in the range of 1:4 to 1:1. It must be understood, however, that larger amounts of the monoacyl component greater than 1:5, or in some cases MAPC on its own may be employed for obtaining maximal bioavailability. The micelle forming lipid and the bilayer forming lipid may be in a mixture resulting from deacylation of a phospholipid by means of phospholipase A2. Particularly preferred blends are enzyme modified phospholipids and lecithin of the type used in the food industry containing 60 to 80 mole percent of monoacyl lipid.

The Hydrophilic Medium

The hydrophilic medium normally comprises 5% to 90% by weight, preferably 20% to 80%, more preferably 30% to 60% of the overall composition. It may be a $C_{1-5}$ alkanol eg. ethanol, a polyol eg. glycerol, propylene glycol or polyethylene glycols with molecular weights up to about 1000. The term "hydrophilic medium" is taken to include water-miscible media such as ethoxydiglycol and tetraglycol. These are $C_1$–$C_5$ alkyl or tetrahydrofurfuryl di- or partial ethers of low molecular weight mono- or poly-oxy alkanediols eg diethylene glycol monoethyl ether and tetrahydrofurfuryl alcohol polyethylene glycol ether. It also includes partially water-miscible polar media such as propylene carbonate, propylene glycol diacetate, triacetin and dimethyl iso-sorbide. Compounds of this latter type are classified as water-soluble (Martindale, The Extra Pharmacoepia Edition 31).

The above is not an exclusive list, and most hydrophilic media may be used, providing they are pharmaceutically acceptable and can substantially dissolve/disperse the lipid. They may be present either alone or in any combination.

The preferred hydrophilic medium is chosen from an alkanol and/or at least one polyol. The preferred alkanol is ethanol and the preferred polyol is glycerol and/or propylene glycol. The nature of the active compound will to a large extent determine the amount and the type of hydrophilic medium used, as long as it is water miscible or water soluble within the definition. In some cases, ethanol may be used on its own, whilst in other cases a mixture comprising ethanol, glycerol and propylene glycol may be preferred. In yet other cases, one or a combination of polyol, water miscible hydrophilic solvent eg. ethoxy diglycol, propylene glycol carbonate may be used in place of ethanol as the hydrophilic medium.

The hydrophilic medium in some cases may also be water, with the proviso that the amount of water present is consistent with the retention of the original structure of the composition. Where the lipid blend comprises MAPC solely or in very high proportions, the hydrophilic medium is usually water or a sugar solution and may be present in high amounts. Alternatively, water may be used in combination with another non-aqueous hydrophilic liquid. Compositions with up to about 10% of water are extremely robust and remain physically stable without phase separation.

Biologically Active Compounds

The composition may further comprise at least one biologically active compound which has lipophilic and/or hydrophilic properties. Preferably it is in solution in the composition but it may also be in dispersion.

Examples of biologically active lipophilic compounds include hydrophobic neutral cyclic peptides eg. cyclosporin A, taxol, tacrolimus or a macrolide e.g. a rapamycin, and derivatives thereof.

Lipophilic vitamin compounds, e.g. tretinoin, isotretinoin and vitamin A and other derivatives of vitamin A may be used in compositions for oral or topical administration.

Another unrelated group of compounds which may be used with advantage are antioxidants, e.g. ubiquinone, tocopherols, carotenoids, and bioflavonoids.

Other examples of therapeutic classes of compound, members of which may be carried in the invention to improve delivery are given below.

Antibiotics, antidepressants, antidiabetics, anti-epileptics, antifungals, anti-gout, antihistamines, anti-malarials, antimigraines, antimuscarinics, anti-neoplastics, anti obesity agents, antiprotozoals, antipyretics, anti-virals, anxiolytic, sedatives, hypnotics and anti-psychotics, haemostatics, calcium regulating agents, cardiovascular, chelating agents antidotes, contrast media, corticosteroids, cough supressants/expectorants and mucolytics, dermatological agents, diagnostic agents, disinfectants and preservatives, dopaminergic agents, GI agents, general anaesthetics, genetic material, hypothalmic and pituitary hormones, lipid regulating agents, local anaesthetics, nutritional agents and vitamins, parasympathomimetics, prophylactic anti-asthma agents, prostaglandins, radio pharmaceuticals, resistance modifying agents, immunosuppressants, sex hormones, skeletal muscle relaxants, stimulants/anorectics, sympathomimetics, vaccines, immunoglobulins and antisera, xanthines.

Preparation of Compositions

The compositions may be prepared by dissolving or dispersing the lipid and the active compound in the hydrophilic medium to obtain a homogeneous solution or dispersion. These may be in the form of liquid, semi-solid or gel-like compositions, depending on the composition and amount of the lipid and the hydrophilic medium. The amount of hydrophilic medium can often be reduced by using more than one component.

Hydration of the Compositions

On contact with water or other aqueous medium or upon dilution, the compositions have the potential to hydrate. This may take place either in situ before use or in the GI tract after oral administration. Depending on the composition and required application, the preparations may remain substantially intact as a hydrated bolus or disperse rapidly, or more gradually, to yield lipid aggregates. Whilst in many cases, it is important for the biologically active compound to be in molecular dispersion in the lipid aggregates after dilution, in other instances, it may not be necessary for it to be substantially associated with the lipid aggregates. In such cases, the active compound may either be in solution or micro suspension in the aqueous medium.

The term lipid aggregates is used here to describe a combination of vesicular and non-vesicular structures e.g. liposomes, various species of mixed micelles and micelles. They are all structured assemblies. Microemulsioh droplets are not included in the definition.

Dispersibility and the different types of aggregate structures formed-depend on a number of factors e.g. the relative amount and the type of diacyl to monoacyl lipid and hydrophilic medium, pH, viscosity and the presence of other components e.g. polymers and surfactants.

The lipid aggregates formed on dilution, from EML or MAPC blended with diacylphospholipid are mixtures comprising vesicles, various species of mixed micelles and micelles. Generally, when the proportion of monoacyl phospholipid predominates, the equilibrium mixture consists mostly of micelle forms, which appear transparent and are generally well below 100 nm in diameter. If the proportion of diacyl phospholipids is sufficiently high, vesicle formation is favoured. Dispersions containing mostly vesicle forms tend to be turbid and the aggregates are generally somewhat greater than 100 nm.

The prior art on phospholipids in drug delivery, is mostly concerned with liposome formation and entrapment, with strong emphasis on structure and particle size characteristics. It was the perceived wisdom that these parameters must be closely controlled. In sharp contrast, the present invention is mainly concerned with the capability of monoacyl membrane lipids, particularly monoacyl phospholipids in combination with diacyl phospholipids, or EML, to improve the bioavailability of poorly absorbed compounds. The surprising finding that the compositions may convert to equilibrium mixtures comprising a combination of lipid aggregates, also sets this invention apart from the prior art.

It must be appreciated that spontaneous dispersion into lipid aggregates, or indeed the type of lipid aggregates formed on dilution, is not an essential feature of the invention. In some instances, it may be preferable to maintain the composition in the form of a structured gel, either on its own or inside a hydratable shell. The composition or its diluted/final dispersed form may also be suspended in an external milieu surrounding or in intimate contact with a tissue/organ, mucosal membrane, or skin, from which the active compound may diffuse out.

The dispersed form of the composition may be obtained in situ by the addition of water or other aqueous medium prior to use, or alternatively the compositions may be administered in unit dosage form in gelatin capsules or the like. Additionally the capsules may be enteric coated or protected so that dispersion mainly takes place in the contents of the small intestines or lower in the gastrointestinal tract eg. colon. On contact with the gastric or intestinal fluids, the contents of the capsule may hydrate initially to form a gel. Where the active compound may not have sufficient storage stability in aqueous or hydrophilic medium, it may be added extemporaneously as a powder or suspension to the lipid compositions in situ, to form a structured gel or a suspension of lipid aggregates for administration.

Polymers

Polymers may influence the dispersion characteristics of the compositions, which surprisingly affects lipid-drug association in this invention. This fact is of particular importance in liquid oral dosage forms. Examples of polymers that affect hydration properties include cellulose derivatives, acrylic and methacrylic polymers, polyglycolic acid, polyethylenes, polypropylenes, polyhydroxybutyrates, etc. Preferably, the polymer is soluble in the hydrophilic medium or in the composition.

Particularly preferred examples are acrylic and methacrylic polymers sold under the brand name Eudragit. Different grades with swelling properties that may be time or pH dependent are available, allowing for control of these parameters in the compositions. The facility to control the hydration, and release of a biologically active compound from a liquid formulation held inside a shell is an unexpected bonus. In some cases, water soluble polymers may also be used in those compositions that contain water. Examples of such polymers are the natural gums, hydroxy propyl methyl cellulose, modified starches, alginates, carboxy vinyl copolymer etc.

The amount of polymer, where used, usually need not exceed 10% by weight of the composition, preferably up to 5%, most preferably between 0.5% to 3%.

Surfactants

The presence of suitable surfactants may also enhance dispersibility. Suitable surfactants include nonionic, anionic, cationic and combinations thereof. Nonionic surfactants are preferred. In addition, other excipients and stabilisers such as inorganic thickeners, antioxidants, flavourings, antimicrobial agents, buffering agents, colouring agents and sweetening agents may be included.

Other stabilising agents such as antioxidants and buffering agents may also be incorporated into the compositions as required to enhance the shelf life. Examples of antioxidants include: ascorbic acid, ascorbyl palmitate, butylated hydroxy anisole, butylated hydroxy toulene, a tocopherol or its derivatives. Stabilising agents or buffering agents should be incorporated at a level sufficient to maintain the pH of the composition within the range 4-8, preferably between 5 and 7.

Oils and free fatty acids often present as by products or impurities in the phospholipids, may also be included as long as their presence is insufficient to play a functional role in the formulation.

Methods of Administration

Although the invention is ideally suited for oral administration, it must be understood that the compositions may also be administered by any of the methods known in the art. Thus, by appropriate selection of suitable components and presentation concomitant with the route and type of application, the compositions may be given by parenteral administration or for tissue wash-out and irrigation purposes following surgical procedures. They may be used in pulmonary delivery, by inhalation in pressurised metered inhalers or by nebulisation after in situ reconstitution. Topical formulations including creams, ointments, gels and lotions for skin and mucosal surfaces and transdermal patches are all within the claims of this invention, and may be easily formulated by those skilled in the art.

EXAMPLES

The invention will now be illustrated below, by way of example and not by way of limitation upon the scope and ambit of the invention.

Dispersibility Measurements 0.4 ml of a fluid composition was added to 40 ml of 0.1 M HCl in 100 ml Duran flask held in a flask-shaker (SF1) set at 250 oscillations per minute under ambient conditions. The time taken for the composition to disperse was recorded in each case.

Analytical Filtration

Analytical filtration is a method for determining the amount of an unassociated hydrophobic compound in a dispersion. The technique involves filtering the dispersion through a pre-weighed 200 nm polycarbonate filter supported in a steel filter holder. This filter is subsequently flushed with 10 ml of filtered deionised water to remove any lipid on the surface of the filter. The filter is carefully air-dried and re-weighed. To determine the amount of unassociated drug, the pre-filtration filter weight is subtracted from the post-filtration filter weight. To calculate the percentage of unassociated hydrophobic compound, this difference is divided by the amount of hydrophobic compound in the dispersion.

Example 1

18 parts of analytically pure soya PC, 27 parts of analytically pure MAPC, and 10 parts of cyclosporin A (cyA) were dispersed in 22.5 parts of ethanol. To this slurry 22.5 parts of glycerol was added. A flowable, optically clear solution resulted after equilibrating the mixture for 24 hours.

0.200 g of the above composition was dispersed in 10 ml of filtered deionised water at room temperature and yielded EML aggregates below 100 nm Z average diameter measured in a Malvern Autosizer. 10 g of this aqueous dispersion was analytically filtered through a pre-weighed 200 nm polycarbonate filter as described above. The percentage of unassociated cyA was found to be less than 1% by weight.

Example 2

The fractionated EML blend used in this example was obtained from soya and had a PC:MAPC weight ratio of approximately 60:40. 45 parts of EML and 5 parts parts of cyA were dispersed in 12.5 parts of ethanol in a glass container. To this slurry 18.75 parts of propylene glycol and 18.75 parts of glycerol were added and equilibrated for 48 hours at room temperature to generate a homogenous liquid composition.

0.8 g of the liquid composition was dispersed in 19.2 g of deionised water. A 10 g aliquot of the resultant turbid dispersion containing EML aggregates was analytically filtered through a pre-weighed 200 nm polycarbonate filter. The percentage of unassociated cyA was determined gravimetrically and was found to be less than 0.5% by weight. No precipitation was evident when this filter was examined under the light microscope at a magnification of ×100. The EML aggregates had a Z average diameter about 390 nm using a Malvern Autosizer.

Example 3

18 parts of purified soya PC, 27 parts of purified soya MAPC and 10 parts of cyA were dispersed in 11.25 parts of ethanol in a closed vessel. To this slurry, 22.5 parts of propylene glycol and 11.25 parts of glycerol were added. After equilibrating the mixture for 24 hours an optically clear solution was produced.

0.200 g of this fluid composition was dispersed in 10 ml of deionised water. This slightly turbid dispersion of EML aggregates was analytically filtered through a pre-weighed 200 nm polycarbonate filter. After air drying this filter, the filter was re-weighed and examined under a light microscope. The percentage of unassociated cyA was found to be less than 1% by weight. No precipitation was observed when the filter was examined under the light microscope at a magnification of ×100.

Example 4

4.5 kg of a commercial grade of refined and chromatographically fractionated EML, (with a PC:MAPC weight ratio of 30:60) and 0.9 kg of cyA were dissolved in 2.0 kg of absolute ethanol in a closed vessel. To this slurry 0.5 kg of propylene carbonate and 2.0 kg of glycerol were added. The resultant slurry was heated at approximately 55° C. until the lipid and cyA had fully dispersed. The above fill solution was filled successfully into oblong soft gelatin capsules (size 20) each containing 100 mg of cyA. The capsules were dried and blister packed.

The chemical stability of the fill material was determined and it was found to be both chemically and physically stable after 6 months storage under accelerated stability testing conditions (40° C.).

Example 5

10 parts of cyA, 55 parts of a commercial grade of EML similar to that used in Example 4, containing 30:60 PC:MAPC, 17.5 parts of ethanol, 12 parts of propylene glycol, 5 parts of glycerol and 5 parts of water were heated to 40° C. in a sealed 100 ml Duran flask overnight until an optically clear fluid solution was obtained.

0.4 ml of the composition was added to 40 ml of 0.1 M HCl in a Duran flask and tested for dispersibility as described. The composition took 90 minutes to fully disperse. Analytical filtration of the dispersion gave a cyclosporin association >89%.

A 5 kg batch was produced and filled successfully into oblong soft gelatin capsules (size 20) each containing 100 mg of cyA. The capsules were dried and blister packed.

Example 6

10 parts of cyA, 55 parts of EML (30:60 PC:MAPC) used in Example 4, 2 parts of Eudragit L100-55, 17.5 parts of absolute ethanol, 12 parts of propylene glycol, 5 parts of glycerol and 5 parts of water were added to a glass container, and heated at 50° C. for 48 hrs to produce an optically clear solution.

The composition hydrated initially to form a gel-like mass, which took 120 minutes to disperse fully into EML aggregates when it was tested, using the procedure described, in simulated gastric fluid. Analytical filtration of the translucent dispersion at alkaline pH indicated a molecular association >99%. The Z average diameter of the EML aggregates was below 100 nm, measured using a Malvern Autosizer.

A 5 kg batch was produced and filled successfully into oblong soft gelatin capsules (size 20) each containing 100 mg of cyA. The capsules were dried and blister packed.

Example 7 (Reference)

55 parts of soya PC and 10 parts of cyA were accurately weighed into a glass container along with 12 parts of propylene glycol, 17.5 parts of ethanol, 5 parts of glycerol and 5 parts of water. Although this composition has identical lipid:drug:hydrophilic weight ratios to Example 5 & 6, it phase separated and was unstable. Thus, a dilution assessment was not carried out.

This example illustrates the serious limitation of using diacyl phospholipid, eg. PC on its own, in the absence of MAPC, to form stable compositions.

Example 8 (Reference)

A co-solvent formulation of cyA without EML was produced by dissolving 10 parts of cyA in a hydrophilic medium comprising 12 parts of propylene glycol, 17.5 parts of ethanol, 5 parts of water and 5 parts of glycerol in a glass vessel, to give an optically clear colourless solution.

The composition was diluted by adding 0.1 g of the solution to 10 ml of deionised water. Upon contact with the water a coarse white precipitate was produced which rapidly sedimented to the bottom of the test tube.

Examples 7 & 8 highlight the important role of MAPC or EML to produce physically stable compositions according to the invention.

Example 9

In this example a composition containing 10% by weight of MAPC was employed. The phospholipid mixture was obtained by blending an enzyme modified lipid from Example 4 (30/60 PC:MAPC) with purified soya PC to obtain the required level of MAPC.

10 parts of the EML blend and 10 parts of cyA were accurately weighed into a glass container along with 40 parts of propylene glycol, 35 parts of ethanol and 5 parts of water. The composition was an optically clear yellow solution.

0.2 g of this formulation was diluted with 10 ml of deionised water to produce a cloudy suspension.

Example 10

An elixir of cyA was produced by dissolving 50 parts of refined and chromatographically fractionated EM (PC:MAPC weight ratio of 10:80) and 1 part of cyA in 50 parts of absolute ethanol. The lipid:drug ratio of the composition was 50:1. The resultant composition was a low viscosity optically clear yellow liquid.

To assess the behaviour of the composition upon dilution, 0.5 g was mixed with 2.5 ml of deionised water. The composition dispersed readily to form an optically clear yellow solution. The Z average diameter of the EML aggregates was below 30 nm using the Malvern Autosizer.

Example 11

In this example an EML blend comprising a PC:MAPC weight ratio of 10% MAPC was employed. The EML blend was obtained as in Example 9. A composition comprising 50 parts EML, 1 part cyA, 17.5 parts of ethanol, 15 parts of propylene glycol and 5 parts of water was prepared by dissolving all the components together in a closed vessel at 40° C. This example has a similar lipid:drug ratio to Example 10. However, the proportion of MAPC in the EML blend of Example 11 is lower.

1.77 g of the composition was diluted with 10 ml of deionised water and produced a turbid dispersion of EML aggregates. The z average diameter of the EML aggregates was approximately 1 $\mu$m.

Example 12

0.05 part of vitamin E acetate was added to a formulation comprising 55 parts of EML from Example 4 (PC:MAPC weight ratio 30:60), 5 parts of cyA, 17.5 parts of ethanol, 15 parts of propylene glycol, and 5 parts of water in a glass container. The chemical stability of the composition was monitored over a three month period at 40° C. The formulation was found to be chemically and physically stable throughout the storage period.

Example 13

The composition of Example 12 was prepared, and the pH was adjusted to 6.8 using TRIS buffer. However, the EML used in this composition had a PC:MAPC ratio of 60:40.

The chemical and physical stability of the formulation was tested, and it was found to be stable throughout a three month period.

Example 14

10 parts of cyA, 18 parts of soya PC, 27 parts of MAPC and 10 parts of polyethoxylated sorbitan mono oleate were dispersed in 17.5 parts of absolute ethanol in a suitable vessel. 15 parts of propylene glycol and 5 parts of water were added to the slurry. The composition was heated at approximately 55° C. until the components had fully dispersed to yield an optically clear solution.

0.5 g of the above formulation was dispersed in 25 ml deionised water at room temperature to yield an optically clear colourless dispersion. The association of cyA was found to be greater than 99% by weight. The Z average diameter of the EML aggregates was found to be below 26 nm.

Example 15

9 parts of cyA, 45 parts of EML used in Example 4 (PC:MAPC weight ratio 30:60) and 10 parts of ethoxylated fatty acids (Labrasol) were dispersed in 17.5 parts of ethanol in a glass container. To this slurry 10 parts of propylene glycol and 10 parts of glycerol were added. The resultant slurry was heated at 40° C. until an optically clear yellow solution was produced. This example was suitable for topical application.

0.4 g was diluted with 10 ml of deionised water at room temperature, to yield an optically clear solution. The degree of association was found to be greater than 99%.

Example 16

50 parts of EML from Example 4 (PC:MAPC 30:60) and 5 parts of miconazole were weighed accurately into a glass container. 50 parts of glycofurol and 10 parts of glycerol were added to produce an optically clear yellow solution. The composition may ,be used for topical administration.

0.46 g of the composition was placed into a test tube in 10 ml of water at room temperature. The test tube was placed in a rotator. The composition slowly hydrated to form a viscous gel which took more than 12 hours to hydrate at room temperature. A translucent suspension of EML aggregates with Z average diameter below 100 nm was obtained.

This example was suitable for topical application.

Example 17

This example utilised an EML blend containing 10% MAPC. The composition was produced by blending an EML (30/60 PC:MAPC) with purified soya PC to obtain the desired level of MAPC, as in Example 9.

50 parts of the EML blend (PC:MAPC 90:10) and 2.5 parts of nifedipine were accurately weighed into a glass container. 50 parts of ethoxydiglycol and 5 parts of water were added to dissolve the EML and nifedipine. The composition was a translucent bright yellow liquid.

0.86 g of the above formulation containing 20 mg nifedipine was diluted with 10 ml of deionised water to produce a bright yellow turbid dispersion. The Z average diameter of the EML aggregates was about 1 µm.

The composition of this example was suitable for oral administration.

Example 18

10 parts of a commercial grade of refined but not chromatographically fractionated EML with a diacyl membrane lipid:monoacyl phospholipid ratio of 90:10 (diacyl lipids include PC, PE, PA, PI, PG and glycolipids; the monoacylphospholipids are the monoacyl equivalents), 100 parts of sorbitan monolaurate (Montanox 20FF) and 10 parts of flurbiprofen were dissolved in 40 parts of ethanol, 20 parts of propylene glycol and 20 parts of glycerol. The EML in this example was obtained directly by phospholipase A2 enzyme hydrolysis of a soya lecithin (45% PC) to give a diacyl membrane lipid:monoacyl phospholipid ratio of 90:10. The resulting composition was an optically clear yellow solution.

0.4 g of this dispersion was diluted in 10 ml of water. The formulation dispersed to yield an optically clear colorless solution.

The composition of this example was suitable for oral administration and for topical application.

Example 19

10 parts of EML from Example 4 with a PC:MAPC ratio of 30:60, 10 parts of polyglyceryl oleate and 1 part of flurbiprofen were dissolved in 4 parts of ethanol, 2 parts propylene glycol and 2 parts of glycerol. The composition was an optically clear yellow liquid.

0.58 g of this formulation was diluted with 10 ml of water. The resultant dispersion was a turbid dispersion. The Z average diameter of the EML aggregates was 600 nm.

Example 20

The following example was produced by dispersing 10 parts of EML from Example 4 (PC:MAPC weight ratio of 30:60) and 2 parts of vitamin E acetate in 1 part of ethanol. The sample was heated to 70° C. to produce a viscous liquid. 0.2 g of the semi fluid composition was hand filled into a size 3 white hard gelatine capsule (HGC). Upon cooling to room temperature the fill material solidified to a yellow plug.

0.10 g of the fill was diluted with 10 ml of water to give a turbid dispersion. The Z average diameter using a Malvern Autosizer was found to be 450 nm.

Examples 21, 22, 23

The following examples employ EML dispersed in a hydrophilic medium which is a sugar solution, suitable for delivering water soluble actives. The compositions may be administered directly to the mucosa or tissues. The biologically active compound in these examples is vancomycin HCl, an example of a water soluble compound which has poor oral bioavailability.

The compositions of the EML formulations containing vancomycin HCl are indicated below. Examples 21 and 22 were produced by dispersing the appropriate weight of refined and chromatographically fractionated EML and glucose in water at 50° C. for 48 hours. Example 23 was produced by hydrating the EML in maltitol syrup.

After the EML had hydrated in the hydrophilic medium, the required amount of vancomycin HCl was added and stirred into each of the compositions. The addition may be made extemporaneously, in situ, prior to use.

| Example | Parts of EML (PC/MAPC weight ratio) | Parts of water | Parts of sugar | Parts of vancomycin HCl |
|---|---|---|---|---|
| 21 | 10 (10:80) | 30 | 30 (Glucose) | 1 |
| 22 | 10 (30:60) | 30 | 30 (Glucose) | 1 |
| 23 | 10 (30:60) | — | 60 (Maltitol syrup) | 1 |

The compositions were suitable for oral, mucosal or buccal applications. Composition 21 was a clear viscous yellow liquid which was more fluid than compositions 22 and 23. Compositions 22 and 23 were clear firm structured gels.

Examples 24, 25, 26, 27, 28

A series of EML compositions containing heparin, a water soluble peptide was prepared by hydrating the appropriate weight of refined and chromatographically fractionated EML in deionised water at 50° C. for 48 hours. Following hydration, the appropriate amount of heparin was intimately incorporated into the bulk to form homogenous compositions.

| Example | Parts of EML (PC/MAPC weight ratio) | Parts of water | Parts of heparin |
|---|---|---|---|
| 24 | 10 (10:80) | 39.5 | 0.5 |

-continued

| Example | Parts of EML (PC/MAPC weight ratio) | Parts of water | Parts of heparin |
|---|---|---|---|
| 25 | 10 (30:60) | 39.5 | 0.5 |
| 26 | 5 (30:60) | 44.5 | 0.5 |
| 27 | 2.5 (30:60) | 47.0 | 0.5 |
| 28 | 1.25 (30:60) | 48.25 | 0.5 |

The compositions of Examples 24 & 28 were clear mobile fluids which may be aseptically filtered to obtain sterile preparations. Compositions 25–27 were clear and structured gels. Composition 28 had a mucous-like consistency.

Example 29

20 parts of purified MAPC and 2 parts of Vitamin A propionate were dispersed in 20 parts of ethanol and 5 parts of water to obtain a clear solution.

0.41 g of the composition was dispersed in 10 ml of deionised water. A clear dispersion was obtained. This example illustrates the use of 100% MAPC with a hydrophilic medium to improve the bioavailability of Vitamin A.

Example 30

To evaluate bioavailability, compositions according to Examples 5 and 6 were administered to 5 and 4 beagle dogs respectively. The amount of cyA administered in each case was 100 mg contained in 2×500 mg gelatine capsules with 50 mg cyA in each capsule. Blood samples were taken from the fore-legs after 1, 2, 4, 6, 8, 12 and 24 hours post administration and assayed for cyA using a non-specific radioimmune assay (RIA). The blood concentration of cyA obtained with the comparator (Neoral) is also shown on the same graph (FIG. 1).

As can be seen in FIG. 1, the compositions of the invention were shown to have a high bioavailability, matching that of the comparator product. The AUC's of the two compositions tested were similar to the comparator product which suggested that the bioavailabilities were similar. The Cmax of the formulations containing EML (Examples 5 and 6) was slightly higher than the comparator formulation.

However, in both the formulations containing EML, the CV (coefficient of variation) for the AUC and Cmax was remarkably low. This indicates that the extent and rate of cyA absorption from the two compositions according to the invention were remarkably reproducible and less variable.

| Formulation | AUC | CV % | Cmax | CV % |
|---|---|---|---|---|
| Example 5 | 10295 | 15.8 | 1706 | 17.66 |
| Example 6 | 10068 | 9.7 | 1910 | 10.2 |
| Comparator | 10531 | 35.3 | 1502 | 33.2 |

What is claimed is:

1. A unit dosage form of a biologically active compound for delivering said compound to a living organism, said dosage form comprising:
   the biologically active compound;
   a mixture of a bilayer-forming diacyl phospholipid with at least one micelle-forming monoacyl phospholipid, said mixture being obtained from enzymatic deacylation of a membrane phospholipid and said bilayer-forming diacyl phospholipid and said micelle-forming monoacyl phospholipid having a molar ratio in the range of 1:5 to 25:1; and 5% to 90% by weight of a mixture of a water-miscible hydrophilic medium which is pharmaceutically acceptable and a polyol, said mixture being capable of dissolving both the biologically active compound and the micelle-forming phospholipid, thus forming a homogeneous liquid, gel or semi-solid that has the property of yielding dispersed lipid aggregates upon contact or further dilution with an aqueous medium.

2. The dosage form of claim 1, wherein the micelle-forming monoacyl phospholipid comprises monoacyl phosphatidyl choline.

3. The dosage form of claim 1, wherein the molar ratio of said bilayer-forming diacyl phospholipid and said micelle-forming monoacyl phospholipid is in the range of 1:4 to 1:1.

4. The dosage form of claim 1, wherein the bilayer-forming phospholipid comprises phosphatidyl ethanolamine, phosphatidyl glycerol, phosphatidyl inositol, phosphatidyl serine, sphingoamyelin or sphingolipid, wherein the sphingolipid is a sphingophospholipid.

5. The dosage form of claim 1, wherein the bilayer-forming phospholipid comprises phosphatidyl choline.

6. The dosage form of claim 1, wherein the mixture of monoacyl and diacyl phospholipids contains 60–80 mole % monoacyl phospholipid.

7. The dosage form of claim 1, wherein said membrane phospholipid is a lecithin.

8. The dosage form of claim 7, wherein said lecithin is a chromatographically fractionated lecithin.

9. The dosage form of claim 1, wherein the hydrophilic medium comprises 20–80 wt % based on the weight of the composition.

10. The dosage form of claim 1, wherein the hydrophilic medium comprises 30–60 wt % based on the weight of the composition.

11. The dosage form of claim 1, wherein the hydrophilic medium comprises a solution of a mono-saccharide or disaccharide sugar.

12. The dosage form of claim 1, wherein the alkanol is ethanol.

13. The dosage form of claim 1, wherein the polyol is glycerol, propylene glycol, polyethylene glycol or a mixture of any of them.

14. The dosage form of claim 1, wherein the hydrophilic medium further comprises a partially water-miscible polar material.

15. The dosage form of claim 1, wherein the partially water-miscible polar material is selected from the group consisting of dimethylisosorbide, ethoxyglycol, glycofurol, propylene carbonate, propylene glycol diacetate, and triacetin.

16. The dosage form of claim 1, wherein there is present at least 0.1 parts by weight of ethanol and 0.1 parts by weight of polyol per part by weight of lipid.

17. The dosage form of claim 1, wherein the biologically active compound is selected from the group consisting of analgesics, anti-inflammatory agents, anthelmintics, antibiotics, antidepressants, antidiabetics, anti-epileptics, antifungals, anti-gout, antihistamines, anti-malarials, antimigraines, antimuscarinics, cytotoxic agents, stimulants and anoretics, antiprotozoals, antipyretics, anti-virals, anxiolytic, sedatives, hypnotics, anti-psychotics, haemostatics, calcium regulating agents, cardiovascular, chelating agents and antidotes, contrast media, corticosteroids, cough suppressants/expectorants, mucolytics, dermatological agents, diagnostic agents, disinfectants, preservatives, dopaminergic agents, gastro-intestinal (GI) agents, anaesthetics, genetic material, hypothalmic and pituitary hormones, lipid regulating agents, local anaesthetics, nutritional agents, vitamins, parasympathomimetics, prophylactic anti-asthma agents, prostaglandins, radio pharmaceuticals, immunosuppressants, sex hormones, skeletal muscle relaxants, stimulants/anorectics, sympathomimetics, vaccines, immunoglobulins, antisera, and xanthines.

18. The dosage form of claim 1, wherein the biologically active compound is a lipophilic compound.

19. The dosage form of claim 1, wherein the biologically active compound is a hydrophilic compound.

20. The dosage form of claim 1, wherein the biologically active compound is a hydrophilic neutral cyclic peptide.

21. The dosage form of claim 1, wherein the compound is a cyclosporin.

22. The dosage form of claim 21, wherein the cyclosporin is cyclosporin A.

23. The dosage form of claim 1, wherein the biologically active compound is taxol, tacrolimus, or rapamycin.

24. The dosage form of claim 1, wherein the biologically active compound is an antioxidant.

25. The dosage form of claim 24, wherein the antioxidant is ubiquinone, a tocopherol, carotenoid or flavenoid.

26. The dosage form of claim 1, wherein the biologically active compound is a water-soluble peptide.

27. The dosage form of claim 26, wherein the peptide is heparin.

28. The dosage form of claim 1, wherein the biologically active compound is a lipophilic vitamin compound.

29. The dosage form of claim 28, wherein the lipophilic vitamin compound is selected from the group consisting of tretinoin, iso-tretinoin, and vitamin A.

30. The dosage form of claim 1, wherein said composition further comprises a polymer.

31. The dosage form of claim 30, wherein the polymer is selected from the group consisting of cellulose derivatives, acrylic polymers, methacrylic polymers, polyglycolic acid, polyethylenes, polypropylenes, polyhydroxybutyrates, and combinations thereof.

32. The dosage form of claim 30, wherein the polymer comprises 0.5–10 wt % based on the weight of the composition.

33. The dosage form of claim 32, further comprising a surfactant.

34. The dosage form of claim 33, wherein the surfactant is non-ionic.

35. The dosage form of claim 34, wherein the surfactant is an ethoxylated derivatised fatty acid and/or a polyglyceryl ester.

36. The dosage form of claim 1, further comprising at least one material selected from preservatives, flavorings, organic thickeners, antioxidants, flavorings, anti-microbial agents, buffering agents, coloring agents, and sweetening agents.

37. The dosage form of claim 1, wherein the composition is fluid at room temperature.

38. The dosage form of claim 1, wherein the composition is fluid at an elevated temperature.

39. The dosage form of claim 1, wherein the composition is sterile.

40. The dosage form of claim 1, wherein the dosage form is comprised within soft gelatin capsules.

41. The dosage form of claim 1, wherein the dosage form is comprised within hard gelatine capsules.

42. The dosage form of claim 1, wherein the dosage form is comprised within gelatin capsules that are enteric coated or protected so that release of the contents takes place in the small intestine or lower in the gastro-intestinal tract.

43. The dosage form of claim 40, wherein the composition further comprises an effective amount of a polymer for retarding hydration of the contents in the gastro-intestinal tract.

44. The dosage form of claim 43, wherein the polymer is effective for prolonging release of the biologically active compound in the small intestine or in the colon.

45. A liquid composition comprising:
(a) a mixture of a bilayer-forming diacyl phospholipid with at least one micelle-forming monoacyl phospholipid; and
(b) ethanol in an amount effective to mobilize the lipids; and/or
(c) a polyol or a further pharmaceutically acceptable hydrophilic medium in an amount effective to maintain the lipids in solution at room temperature;
said micelle-forming phospholipid and said bilayer-forming phospholipid are in a mixture resulting from enzymatic deacylation of a membrane phospholipid, said bilayer-forming diacyl phospholipid and said micelle-forming monoacyl phospholipid having a molar ratio in the range of 1:5 to 25:1, or are a blend of said deacylated phospholipid with pure micelle-forming phospholipid or membrane-forming phospholipid.

46. A liquid composition comprising:
(a) a mixture of membrane phospholipids which comprises a micelle-forming monoacyl phospholipid and a bilayer-forming diacyl phospholipid; and
(b) water;
said micelle-forming phospholipid and said bilayer-forming phospholipid being in a mixture resulting from enzymatic deacylation of a membrane phospholipid, said bilayer-forming diacyl phospholipid and said micelle-forming monoacyl phospholipid having a molar ratio in the range of 1:5 to 25:1, or being a blend of said deacylated phospholipid with a pure micelle-forming phospholipid or membrane-forming phospholipid.

47. The dosage form of claim 1, wherein said water-miscible hydrophilic medium is selected from the group consisting of a $C_1$–$C_5$ alkanol, a further water-miscible hydrophilic solvent which is pharmaceutically acceptable, a sugar solution, water, and mixtures thereof.

48. The composition of claim 45, further comprising a biologically active compound.

49. A method of producing the composition of claim 45, wherein said method comprises mixing said micelle-forming monoacyl phospholipid with said bilayer-forming diacyl phospholipid, wherein said mixture is obtained by the enzymatic deacylation of a membrane phospholipid; and mixing said mixture of phospholipids with said ethanol and/or said polyol.

50. The composition of claim 45, wherein said composition is formulated for oral, pulmonary, topical, mucosal or tissue irrigation administration.

51. The composition of claim 50, wherein said composition is comprised within a capsule for oral administration.

52. The composition of claim 46, further comprising a biologically active compound.

53. A unit dosage form of a biologically active hydrophilic compound for delivering said compound to a living organism, said composition comprising:

the biologically active compound;

at least one micelle-forming monoacyl phospholipid in admixture with a bilayer-forming diacyl phospholipid, said admixture of phospholipids being enzymatically derived, and said bilayer-forming diacyl phospholipid and said micelle-forming monoacyl phospholipid in said admixture having a molar ratio in the range of 1:5 to 25:1; and a hydrophilic medium that dissolves both the biologically active compound and the admixture of phospholipids to form a homogenous liquid, gel or semi-solid that has the property of yielding dispersed lipid aggregates upon contact or further dilution with an aqueous medium.

54. A composition for topical application for delivering a biologically active compound to a living organism, said composition comprising:

the biologically active compound;

at least one micelle-forming monoacyl phospholipid in admixture with a bilayer-forming diacyl phospholipid, said admixture of phospholipids being enzymatically derived, and said bilayer-forming diacyl phospholipid and said micelle-forming monoacyl phospholipid in said admixture having a molar ratio in the range of 1:5 to 25:1; and a hydrophilic medium that dissolves both, the biologically active compound and the admixture of phospholipids, to form a homogeneous liquid, gel or semi-solid that has the property of yielding dispersed lipid aggregates upon contact or further dilution with an aqueous medium.

* * * * *